United States Patent [19]

Foulds et al.

[11] Patent Number: 5,124,253
[45] Date of Patent: Jun. 23, 1992

[54] DRY STRIP ELEMENT FOR THE ELECTROCHEMICAL DETECTION OF THEOPHYLLINE

[75] Inventors: Nicola C. Foulds, Wantage; Jane M. Wilshere, Abingdon, both of Great Britain

[73] Assignee: Medisense, Inc., Cambridge, Mass.

[21] Appl. No.: 413,178

[22] Filed: Sep. 27, 1989

[30] Foreign Application Priority Data

Sep. 28, 1988 [GB] United Kingdom ............... 8822738

[51] Int. Cl.$^5$ ............................................... C12Q 1/42
[52] U.S. Cl. ........................................ 435/21; 435/817
[58] Field of Search ............... 435/21, 288, 291, 805, 435/817, 19; 204/403

[56] References Cited

U.S. PATENT DOCUMENTS

| | | | |
|---|---|---|---|
| 4,782,016 | 11/1988 | Norton | 435/21 |
| 4,782,017 | 11/1988 | Frickey et al. | 435/21 |
| 4,806,470 | 2/1989 | Frickey et al. | 435/21 |
| 4,830,959 | 5/1989 | McNeil et al. | 435/817 |
| 4,897,173 | 1/1990 | Nankai et al. | 435/817 |
| 4,948,727 | 8/1990 | Cass et al. | 435/18 |
| 5,028,528 | 7/1991 | Frickey et al. | 435/21 |

FOREIGN PATENT DOCUMENTS

| | | |
|---|---|---|
| 0188372 | 1/1986 | European Pat. Off. . |
| 0258034 | 8/1987 | European Pat. Off. . |
| 0258035 | 8/1987 | European Pat. Off. . |

OTHER PUBLICATIONS

Frew et al., J. Electroanal. Chem 266:309–316 (1989).

*Primary Examiner*—Robert J. Warden
*Assistant Examiner*—Matthew W. Hanley
*Attorney, Agent, or Firm*—Fish & Richardson

[57] ABSTRACT

A dry strip element for use in an electrochemical assay for determining theophylline in a sample, the test element carrying a working electrode and a reference electrode and separately carrying at the working electrode an alkaline phosphatase and an electroinactive phosphate ester which is a substrate for the alkaline phosphatase and from which an electroactive compound can be released by catalytic activity of the alkaline phosphatase.

9 Claims, 3 Drawing Sheets

CYCLIC VOLTAMMOGRAMS OF p-AMINOPHENYL PHOSPHATE

CYCLIC VOLTAMMOGRAMS OF p-AMINOPHENOL

DRY STRIP ELEMENT FOR THE ELECTROCHEMICAL DETECTION OF THEOPHYLLINE

BACKGROUND OF THE INVENTION

Theophylline is a bronchodilator and respiratory stimulant that is effective in the treatment of acute and chronic asthma, Cheyne-Stokes respirations, and apnea/bradycardia episodes in newborn infants. It is also used as an adjunct in the treatment of congestive heart failure and acute pulmonary edema. The most important current use of theophylline is as a prophylactic agent for controlling the symptoms of chronic asthma.

The therapeutic range for theophylline is relatively narrow, around 10–20 μg/ml (55–110 μM). Since the metabolism of theophylline varies from individual to individual, close monitoring is needed in order to avoid harmful side-effects caused by overdoses. The need for a quick, easy-to-use device which can monitor the narrow theophylline therapeutic range has been recognized for some time. Such devices have to cover not only the therapeutic range, but also higher and lower levels; in cases of toxicity, levels as high as 60 μg/ml (330 μM) may be encountered.

There are many current methods for measuring theophylline, including chromatographic and immunoassay procedures. In any assay method, advantage is taken of the knowledge that theophylline can be determined by measuring its inhibition of alkaline phosphatase. However, when assaying human biological fluids in this manner, endogenous alkaline phosphatase can effect the assay and render results inaccurate.

In EP 188372, a method of eliminating the effect of endogenous alkaline phosphatase is described. Theophylline is a very potent inhibitor of certain isozymes of alkaline phosphatase, particularly that obtained from bovine liver. At a pH less than 9, this isozyme exhibits greater catalytic activity than isozymes present in human serum. When bovine liver alkaline phosphatase and a substrate, p-nitrophenylphosphate, are present in a layered strip along with a buffer to give the lower pH, the application of a sample to the strip results in an enzyme activity at pH 9 or less, and gives a color intensity that is inversely proportional to the concentration of theophylline in the sample. The color is read from the back of the strip using a reflectance photometer.

A modified system is described in EP 258034, in which the buffer is in a porous spreading zone. EP 258035 describes another modification, in which a greater quantity of isoenzyme is employed. Both of these modifications are intended to minimize the effect of endogenous alkaline phosphatase, among other objects.

OBJECTS OF THE INVENTION

The present invention seeks to provide a radically different theophylline assay based on an electrochemical determination. A further object of the invention is the provision of test elements for use in a novel assay.

SUMMARY OF THE INVENTION

An assay is provided for determining theophylline in a sample such as whole blood. The assay is based upon the generation of an electroactive compound, such as p-aminophenol, from a corresponding phosphate ester by the action of an alkaline phosphatase, see FIG. 1, and the detection of current arising from electrochemical oxidation of the generated electroactive compound. Any theophylline present in the sample inhibits the generation of the electroactive compound and thus results in a correspondingly lower current.

PREFERRED EMBODIMENTS OF THE INVENTION

For preference, the present invention employs a dry strip element, especially a disposable test element, for use in conjunction with a read-out device to which the test element can be connected to give a reading of the theophylline level after application of a sample to the test element. For example, the read-out device can be a hand-held or desk-top instrument.

Figure 1:
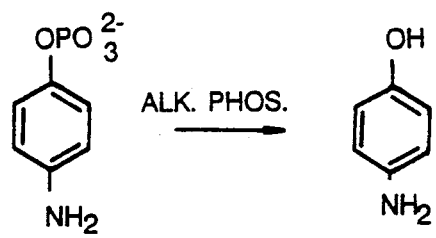
FIG. 1 is a diagram of the alkaline phosphatase catalyzed conversion of p-aminophenyl phosphate to p-aminophenol.
Figure 2:
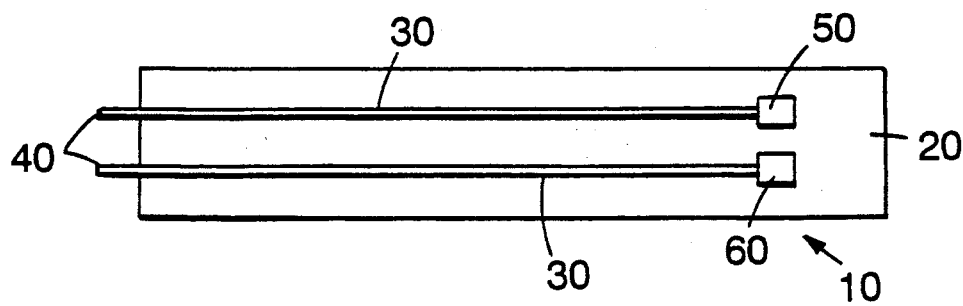
FIG. 2 is a diagram of a test strip.

The test element carries a working electrode and a reference electrode, see FIG. 2. The alkaline phosphatase and the electroinactive phosphate ester are at the working electrode, but are preferably separate from each other, avoiding the risk of interaction before the sample is added. When the sample is added, the liquid brings the substrate into contact with the enzyme along with any theophylline present in the sample. After a predetermined incubation period, such as 60 to 150 seconds, typically 120 seconds, to allow for reaction, a reading can be taken. The reading can be taken by poising the working electrode at a suitable potential, such as 100 to 200 mV, typically 150 mV, and monitoring the resultant current for a set time such as 30 to 60 seconds, typically 45 seconds. By reference to currents generated under standardised conditions with known concentrations of theophylline, the current can be used to give a quantitative value of the theophylline level.

Typically, in the test element, the enzyme and the substrate are in separate carbon-based layers. The respective carbon mixtures are applied to a conductive track of a support, for example in the close proximity of a reference electrode mixture connected to a second track. In this way, a miniaturized sensor is produced which is capable of working with a small sample of blood bridging the electrode areas. The mixtures are suitably applied by screen printing. Suitable enzymes and suitable substrates can be determined by routine experimentation. Bovine liver alkaline phosphatase is the preferred enzyme, and p-aminophenyl phosphate is the preferred substrate. Other candidate substrates include, for example naphthyl phosphate, and 4-ferrocenylaminophenyl phosphate. However, p-aminophenyl phosphate is preferred because of the change in electrochemistry on dephosphorylation (p-aminophenyl phosphate gives an irreversible oxidation wave at around +450 to 500 mV (vs Ag/AgCl)

whereas p-aminophenol exhibits a reversible wave with an $E^{o'}$ of about $-65$ mV). Furthermore the electrochemistry of p-aminophenol is in a potential region where there would be minimal interference from endogenous blood components.

In a particularly preferred embodiment, as shown in FIG. 2, the present invention provides a dry strip sensor 10 which comprises an elongate, electrically-insulating substrate 20 having a pair of longitudinal, substantially parallel, electrically-conducting tracks 30 thereupon, each track, which may be of multilayer construction, being provided at the same end with means for electrical connection 40 to a read-out means and provided with an electrode, one of the electrodes being the reference electrode 50 and the other being the working electrode 60 with enzyme and substrate separate from each other.

More especially, such a sensor is suitably configured in the form of a supporting strip of electrically insulating material such as a synthetic polymer (for instance pvc) carrying at a location between its ends the two electrodes supported on electrically conductive printed tracks. For example, the electrodes can taken the form of two rectangular areas side by side on the strip. Such areas can be configured to be covered by a single drop of blood for testing for theophylline. If desired, non-rectangular electrode areas, for instance diamond-shaped, semicircular, or triangular areas, can be employed to provide an area for optimised contact by a liquid sample.

Although pre-treatment of samples to remove or inactivate endogenous alkaline phosphatase is possible, it is preferred to incorporate in the test element the means to minimise interference by endogenous enzyme. To this end, the present system can employ isozymes effective below pH 9, and a suitable buffer, as described in EP 188372. However, it is greatly preferred to arrange that the enzyme of the test element overlays the substrate, since surprisingly it seems that this arrangement can in itself be sufficient to vitiate the effect of endogenous enzyme.

Thus, in a preferred arrangement, it is not necessary to maintain the pH below 9. Interference from endogenous enzyme is avoided by superposing the enzyme on the substrate. This arrangement is believed to avoid interference by minimizing significant mixing with the added sample during the incubation period.

Blood typically has a pH of 7.4, and the test elements of this invention preferably incorporate a buffer to bring the pH to an alkaline value suited to the enzyme of the test element, such as pH 9 to 10, for instance about pH 9.5. The buffer, such as tris(hydroxymethyl)aminoethane ("tris"), diethanolamine ("DEA"), or 2-amino-2-methyl-1,3-propanediol ("AMPD"), can be incorporated with the enzyme or with the substrate, preferably both.

Further buffering capacity can be provided by incorporating a buffer layer over the enzyme and substrate. For instance, a buffer-impregnated mesh has been found to give good pH adjustment of the sample before it reaches the enzyme and substrate of the test element. Examples of suitable meshes include nylon, polyester, glass fibre and cellulosic meshes. The meshes may be woven or non-woven.

EXAMPLES OF THE INVENTION

The present invention is illustrated by the following examples.

EXAMPLE 1

Preparation of p-Aminophenyl Phosphate

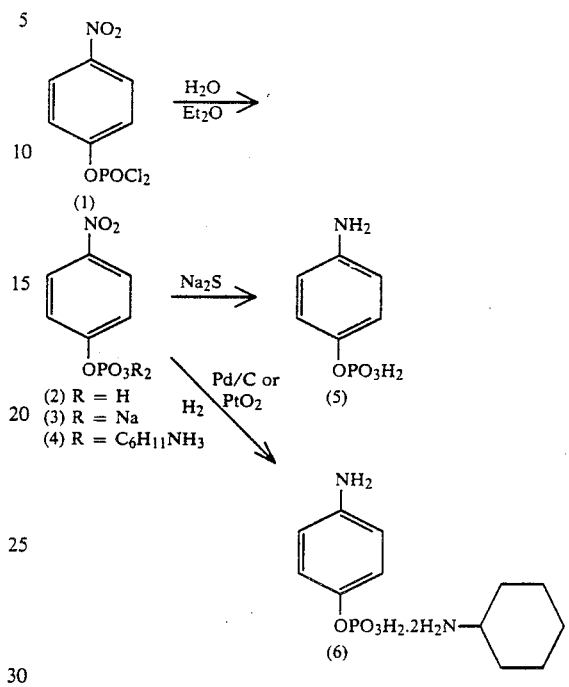

Two synthetic routes to p-aminophenyl phosphate (5) were evaluated. Both are based on the reduction of p-nitrophenyl phosphate which is available from a number of companies as the disodium (3) or bis cyclohexylammonium (4) salt. The free acid (2) may be synthesized in high yield [Rec. Trav. Chim. Pays-Bas, 75 (1956) 378] by simple hydrolysis of the phosphorodichloridate (1) available from Aldrich, and isolated as an oil by evaporation of the solvent and used without further purification.

(i) Zinin reduction p-Nitrophenyl phosphate is subjected to a Zinin reduction using sodium sulphide. The procedure was adapted from a literature method [J. Am. Chem. Soc., 69 (1947) 2112] for the preparation of p-aminophenyl phosphonic acid from the corresponding nitro derivative.

42 g (0.19 mol) of p-nitrophenyl dihydrogen phosphate (2) in 100 ml of water were brought into solution with 10% NaOH solution to pH 9. Sodium sulphide nonahydrate (91.2 g, 0.38 mol) was added and the resulting mixture was heated to 90°–95° C. in an oil bath for 1 hour. The cooled solution was acidified strongly with conc. HCl and then filtered. The acid filtrate was treated with 25% NaOH solution until pH 4–5 and allowed to cool. The monosodium salt of p-aminophenyl phosphate was collected as fluffy white crystals and recrystallized from boiling methanol. Satisfactory analytical data was obtained if the salt was formulated as a pentahydrate. The IR spectrum displayed a strong O—H stretching band in the region 3100–3500 cm$^{-1}$ mpt. 181°–183° C. (decomp).

p-Aminophenyl dihydrogen phosphate (5) was obtained by dissolving the monosodium salt in the minimum amount of water, filtering and then acidifying to pH 3–4 with conc. HCl. A heavy white precipitate was deposited and this was collected on a sinter, washed with EtOH then ether. Upon drying in air, an off-white powder (18.0-23.3 g, 50-65% yield) remained. Mpt. 261°-264° C. (decomp.) [lit. (Z.h. Organ. Khim., 10 (1974) 807) 245°-249° C. (decomp.) (from EtOH)]; m.s.:m/z 139, 109, 80. One spot by TLC analysis on silica gel in a n—BuOH—EtOH—H$_2$O (55:35:10) system—visualisation was by UV, 0.2% ninhydrin in EtOH or alkaline KMnO$_4$.

Catalytic hydrogenation

To a solution of bis (cyclohexylammonium) p-nitrophenyl phosphate (5.0 g, 12 mmol) in 250 ml of methanol was added 30 mg of PtO$_2$ catalyst. Hydrogenation was conducted at room temperature and atmosphere pressure for a period of 18 hours. The catalyst was then removed by filtration. Removal of the solvent from the filtrate under reduced pressure afforded bis (cyclohexylammonium) p-aminophenyl phosphate in quantitative yield. Further purification was unnecessary as judged by TLC, but if required, the compound may be recrystallized form EtOH or MeOH. Mpt. 198°-200° C. (decomp).

Figure 3:
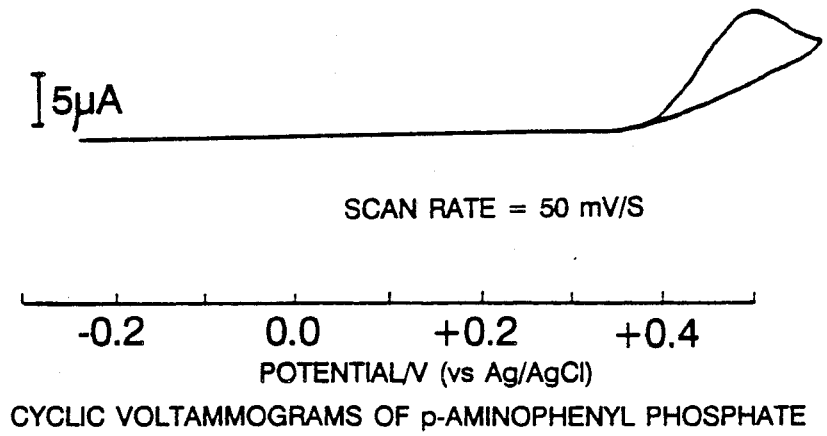
FIG. 3 is a cyclic voltammogram of p-aminophenyl phosphate.
Figure 4:
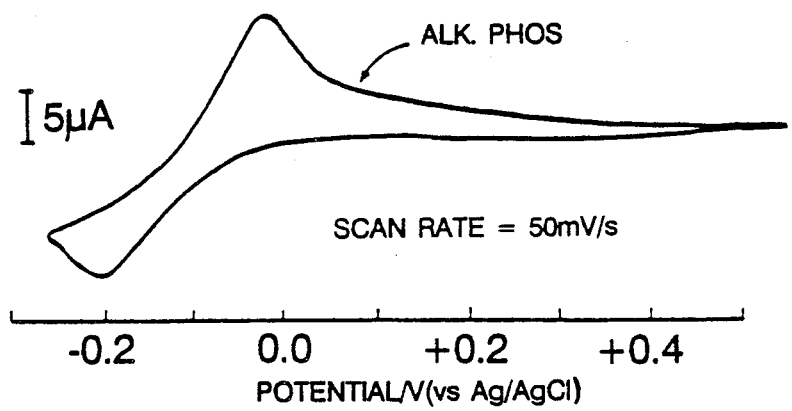
FIG. 4 is a cyclic voltammogram of p-aminophenol.
Figure 5:
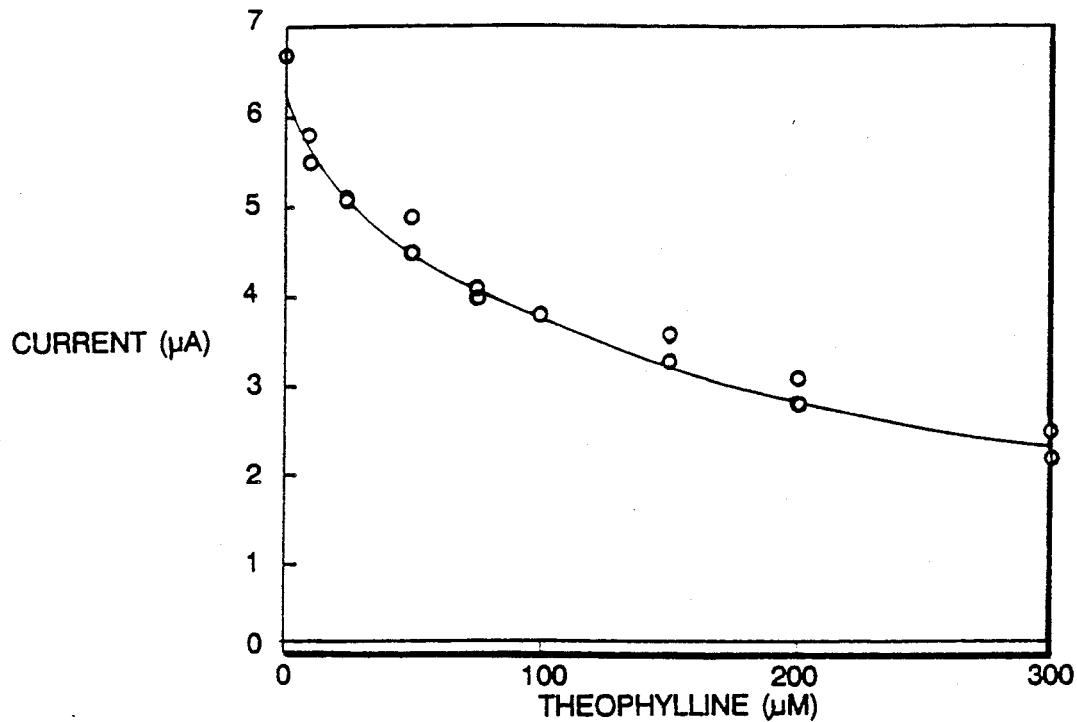
FIG. 5 is a graph of theophylline concentration versus current.
Figure 6:
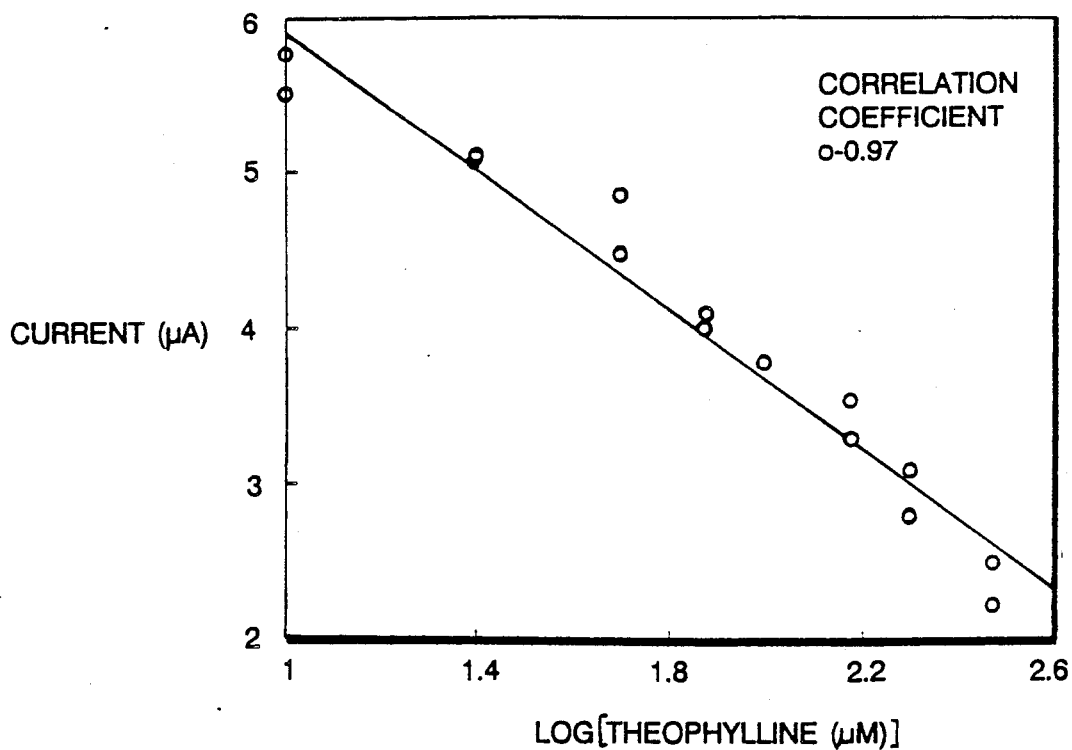
FIG. 6 is a graph of the log theophylline concentration versus current.
Figure 7:
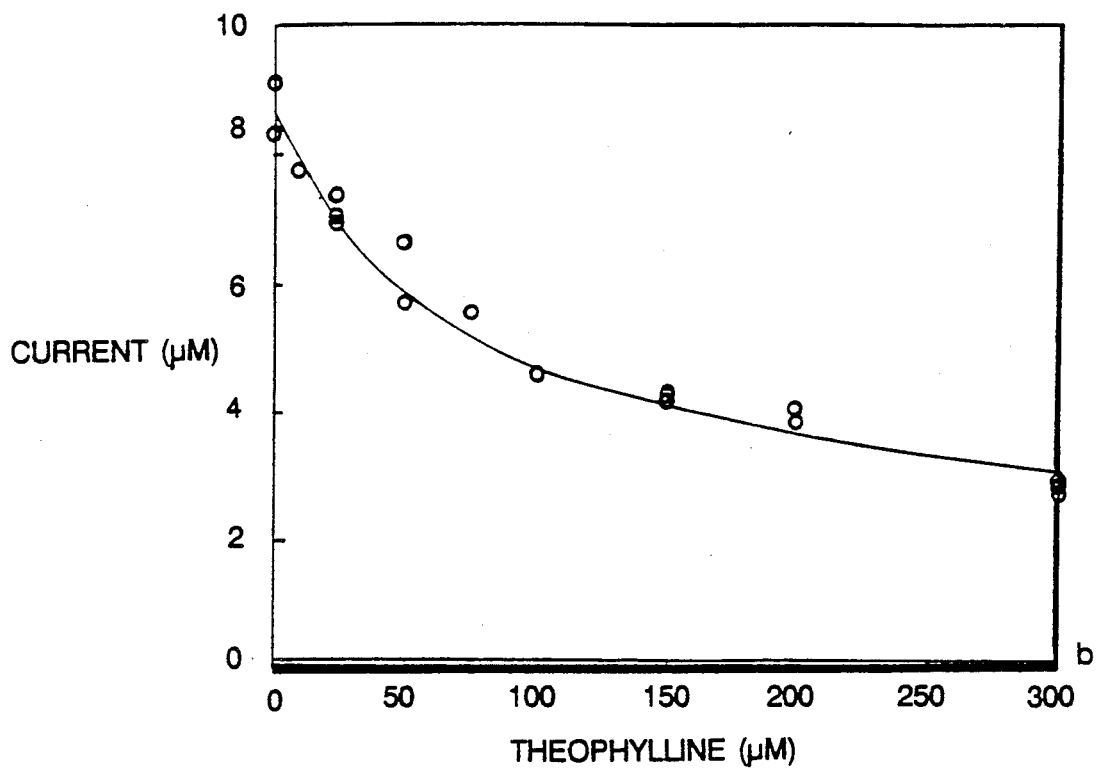
FIG. 7 is a graph of theophylline concentration versus current.
Figure 8:
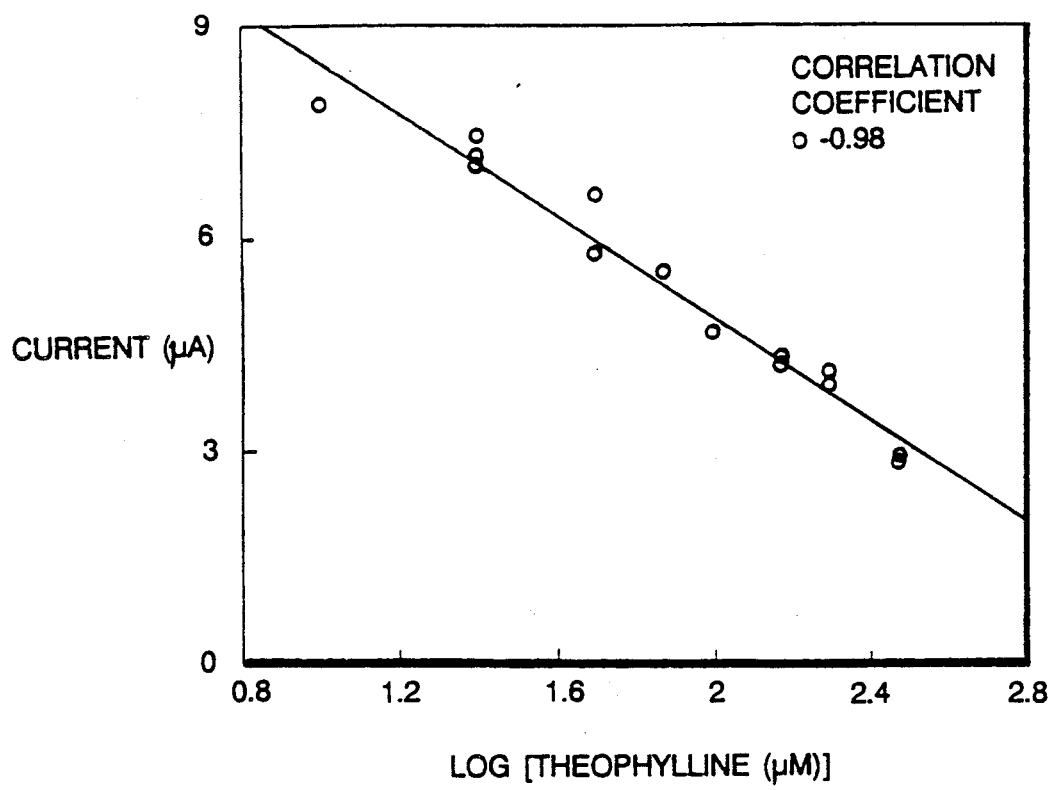
FIG. 8 is a graph of the log of theophylline concentration versus current.

Cyclic voltammograms of p-aminophenyl phosphate before and after incubation with alkaline phosphatase are shown in FIGS. 3 and 4, the lower voltammogram corresponding to post-incubation.

EXAMPLE 2

Multiple test elements were prepared by printing and then subdividing a sheet of pvc plastics material. For the working electrode and the reference electrode of each test element, parallel electrically conducting tracks were laid down and then overprinted. For the reference electrode, an Ag/AgCl mix was used. For the working electrode, two basic print mixes were required, as follows:

Substrate Layer
1.2 g carbon powder
560 mg gelling agent
0.2 ml surfactant
0 to 1.2 g p-aminophenyl phosphate
2.7 ml buffer Enzyme Layer
1.2 g carbon powder
560 mg gelling agent
0.2 ml surfactant
0 to 500 U bovine liver alkaline phosphatase
2.65 ml buffer The substrate layer was printed first, and the enzyme layer applied after thorough drying of the substrate layer.

In some instances, nylon mesh coated with tris buffer was then superimposed.

By routine experiment, it was found that a suitable level of substrate was about 200 mg and a suitable level of enzyme was about 500 U, for the particular size of test elements being manufactured.

Several different buffer conditions for printing the strips, together with different buffers for adjusting the pH of the blood to alkaline values were examined. All these print batches were printed with the inclusion of 500 U of bovine liver alkaline phosphatase in the enzyme mix and 200 mg pAPP in the substrate mix. A summary of the results obtained in given in the following table. In this table, the print conditions refer to the buffer included in the print mix and the test conditions to the 5M buffer that was used to adjust the pH of the blood to alkaline values. The results are displayed as maximum current (i.e. that obtained with no theophylline present) in the top left of each square, and percentage inhibition obtained (for 300 μM theophylline) in the bottom right of each square.

| PRINT CONDITIONS | TEST CONDITIONS (1:12, 5 M buffer:blood) | | | | | |
|---|---|---|---|---|---|---|
| | DEA | AMPO | TRIS | TRIS MESH | | |
| DEA | pH 9.5 | pH 9.8 | pH 9.5 | pH 9.8 | pH 9.1 | pH 9.1 | pH 9.5 |
| 0.1 M, pH 9.5 | 19.7 / 62 | 26.4 / 59 | 7.8 / 50 | 12.3 / 29 | | | |
| 0.5 M, pH 9.8 | | 37.6 / 52 | | 16.2 / 51 | | | |
| AMPO | | | | | | | |
| 0.1 M, pH 9.5 | 16.8 / 71 | | | | 3.4 / 59 | 6.7 / 64 | |
| 0.5 M, pH 9.5 | 32.5 / 57 | | 14.1 / 49 | | | | 10.2 / 49 |
| 0.5 M, pH 9.8 | 42.6 / 67 | | 20.5 / 56 | | | | |
| TRIS | | | | | | | |
| 0.1 M, pH 9.5 | 20.5 / 67 | | 12.8 / 59 | | 4.8 / 57 | 8.6 / 71 | 8.8 / 65 |
| 0.5 M, pH 9.5 | 18.6 / 67 | | 6.6 / 58 | | 5.1 / 53 | 5.1 / 55 | 4.7 / 47 | results displayed in this format- % I is the percentage inhibition caused by 300 μM theophylline.

current (max) / % I $$ie\ \%\ I = \frac{i_{max} - i_{300\ \mu M\ theop}}{i_{max}} \times 100$$

Looking at the table, it can be seen that significantly higher currents are obtained when testing in DEA rather than AMPD of tris and also high pH and higher buffer strength favour high currents, but lower pH's and lower buffer strengths favour good inhibition of the enzyme by the theophylline. Such results were fully consistent with initial studies performed in a homogenous aqueous system.

EXAMPLE 3

Typical calibrations for particularly effective test elements are shown in FIGS. 5, 6, 7, and 8. These calibrations were obtained using strips that were printed in 0.1M AMPD, pH 9.5 (FIGS. 5 and 6) and 0.1M tris, pH 9.5 (FIGS. 7 and 8) and using a nylon mesh that had been coated using 5M tris.

EXAMPLE 4

The possible effect of endogenous alkaline phosphatase was examined.

To 1-day old blood was added 5M DEA, pH 9.5 at a dilution of 1:12. Aliquots were then spiked with alkaline phosphatase to 0.2 U/ml (normal adult), 0.34 U/ml (normal child), and 2.0 U/ml. Theophylline strips printed with 0.1M tris, pH 9.5, 200 mg p-aminophenyl phosphate in the substrate mix and 500 U bovine liver alkaline phosphatase in the enzyme mix, together with otherwise identical strips with no enzyme layer were tested, giving the following results for the current in μA after 45 seconds.

| | current (μA) | | plus DEA and enzyme (U/ml) | | |
|---|---|---|---|---|---|
| | unspiked blood | plus DEA | 0.2 | 0.34 | 2.0 |
| substrate | 0 | 0.35 | 0.95 | 1.2 | 5.6 |
| | 0 | 0.35 | 1.1 | 1.3 | 5.9 |
| substrate | 0.15 | 13.8 | 13.1 | 13.1 | 13.6 |
| plus enzyme | 0.15 | 13.9 | 13.9 | 14.1 | 14.0 |
| | | 14.9 | | | 15.1 |

For the strips with substrate and enzyme, it can be seen that no significant interference occurred with normal or diseased alkaline phosphatase levels.

However, for the substrate-only strips, significant currents are obtained when the blood has been spiked with enzyme. It seems therefore that the printed enzyme layer has the effect of protecting the substrate layer from endogenous enzyme. Significant mixing of the layers with the added blood appears not to occur within the two minute incubation period. Further experimental work supports this view.

We claim:

1. A dry strip element for use in an electrochemical assay method for detecting theophyline, said element comprising a working electrode and a reference electrode and separately comprising at the working electrode an alkaline phosphatase and an electroinactive phosphate ester which is a substrate for the alkaline phosphatase and from which an electroactive compound can be released by catalytic activity of the alkaline phosphatase.

2. A dry strip element according to claim 1, wherein the alkaline phosphatase and the electroinactive phosphate ester are in separate carbon-based layers.

3. A dry strip element according to claim 2, further comprising a support and wherein the carbon-based layers are on a first conductive track of the support and are in sufficiently close proximity to a reference electrode layer on a second conductive track on the support that a sample applied to said element bridges said carbon-based layers and said reference electrode.

4. A dry strip element according to claim 1, which comprises an elongate, electrically-insulating support having a pair of longitudinal, substantially parallel, electrically-conducting tracks thereupon, each track being provided at the same and with means for electrical connection to a read-out means and provided with an electrode, one of the electrodes being the reference electrode and the other being the working electrode with enzyme and substrate separate from each other.

5. A dry strip element according to claim 11, which incorporates a buffer to buffer the pH at 9 to 10 during the assay said buffer being positioned between the region of sample application and the alkaline phosphatase.

6. A dry strip element according to claim 5, wherein a buffer-impregnated mesh overlies the alkaline phosphatase and the phosphate ester.

7. A dry strip element according to claim 11, in which the alkaline phosphatase is positioned so as to protect said substrate from the sample allowing said alkaline phosphatase to be contacted by the sample before the phosphate ester.

8. A dry strip element according to claim 6, wherein the alkaline phosphatase overlies the phosphate ester which in turn overlies the working electrode.

9. A dry strip element according to claim 1, wherein said phosphate ester is p aminophenyl phosphate.

* * * * *

UNITED STATES PATENT AND TRADEMARK OFFICE
CERTIFICATE OF CORRECTION

PATENT NO. : 5,124,253
DATED : June 23, 1992
INVENTOR(S) : Nicola C. Foulds, et al It is certified that error appears in the above-indentified patent and that said Letters Patent is hereby corrected as shown below:

Col. 2, line 15; delete "," and insert therefore --.--

Col. 6, line 10; delete "AMPO" and insert therefore --AMPD--

Col. 6, line 20; delete "AMPO" and insert therefore --AMPD--

Col. 6, line 48; delete "of" and insert therefore --or--

Col. 8, line 22; delete "claim 11" and insert therefore --claim 1--

Col. 8, line 29; delete "claim 11" and insert therefore --claim 1--.

Signed and Sealed this

Fifth Day of October, 1993

Attest:

BRUCE LEHMAN

Attesting Officer

Commissioner of Patents and Trademarks